United States Patent [19]

Vlattas

[11] 4,088,779
[45] May 9, 1978

[54] 9-OXAPROSTAGLANDINS

[75] Inventor: Isidoros Vlattas, Summit, N.J.

[73] Assignee: Ciba-Geigy Corporation, Ardsley, N.Y.

[21] Appl. No.: 729,572

[22] Filed: Oct. 4, 1976

Related U.S. Application Data

[63] Continuation-in-part of Ser. No. 621,904, Oct. 14, 1975, abandoned, which is a continuation-in-part of Ser. No. 516,294, Oct. 21, 1974, abandoned, which is a continuation-in-part of Ser. No. 361,694, May 18, 1973, Pat. No. 3,883,659.

[51] Int. Cl.$^2$ .................. C07D 307/16; A61K 31/34
[52] U.S. Cl. ........................... 424/285; 424/275; 424/278; 424/282; 260/340.3; 260/340.5 P; 260/332.2 A; 260/347.3; 260/347.4; 542/413; 542/400
[58] Field of Search ............ 260/240 R, 347.3, 347.4, 260/340.3, 340.5, 332.2 A; 424/275, 282, 285

[56] References Cited

PUBLICATIONS

Vlattas et al., Tetrahedron Left. 1974, (51/52), pp. 4455–4458.

Primary Examiner—Henry R. Jiles
Assistant Examiner—Bernard Dentz
Attorney, Agent, or Firm—Theodore O. Groeger

[57] ABSTRACT

7-[3α-(3-hydroxy-3-hydrocarbylpropyl, or -1-propenyl, or 1-propynyl)-4-hydroxy-tetrahydro-2β-furyl]-heptanoic or 4-heptenoic acids, esters or salts thereof are stable, prostaglandin-like acting agents.

8 Claims, No Drawings

9-OXAPROSTAGLANDINS

CROSS-REFERENCE TO RELATED APPLICATIONS

This is a continuation-in-part of application Ser. No. 621,904, filed Oct. 14, 1975, which in turn is a continuation-in-part of application Ser. No. 516,294, filed Oct. 21, 1974, (both are now abandoned) which in turn is a continuation-in-part of application Ser. No. 361,694, filed May 18, 1973 (now U.S. Pat. No. 3,883,659).

BACKGROUND OF THE INVENTION

It is known that the natural prostaglandins are very rapidly metabolized to less active or inactive compounds, some even within a few minutes after intravenous administration. Moreover, according to German Pat. No. 2,229,225 lactones are known (formally 9-oxo-10-oxaprostanoic acid derivatives) which are similarly prone to metabolic attack, e.g. under alkaline conditions in the gut. The 9-oxaprostanoic acid derivatives of the invention, however, are chemically and metabolically quite stable compounds which surprisingly exhibit the full spectrum of activity shown by the natural prostaglandins.

SUMMARY OF THE INVENTION

The present invention concerns and has for its object the provision of 7-[3α-(3-hydroxy-3-hydrocarbylpropyl or -1-propenor ynyl)-4-hydroxy-tetrahydro-2β-furyl]-heptanoic or 5-heptenoic acids, more particularly of those corresponding to Formula I

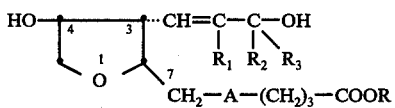

wherein A is ethylene or ethenylene, each of $R_1$ and $R_2$ is hydrogen or lower alkyl, each of R and $R_3$ are an aliphatic, cycloaliphatic, cycloaliphatic-aliphatic or araliphatic radical, or R is hydrogen or one base-equivalent, such as an alkali metal, one equivalent of an alkaline earth metal, ammonium, mono, di or tri-lower alkyl-, or mono-, di- or trihydroxyalkylammonium; or the 1,2-dihydro- or -dehydro derivatives thereof, corresponding pharmaceutical compositions and methods for the preparation and application of these products, which are useful prostaglandin-like acting smooth muscle contractants and abortifacient agents, but more stable than the easily dehydrating prostaglandins of the E series, or hydrolyzable 9-oxo-10-oxaprostanoic acid derivatives.

DESCRIPTION OF THE PREFERRED EMBODIMENTS

An aliphatic radical R or $R_3$ represents preferably lower alkyl, as is the case with $R_1$ and $R_2$, e.g. methyl, ethyl, n- or i-propyl, -butyl, -pentyl, -hexyl or -heptyl; lower alkenyl, e.g. allyl or methallyl; or lower alkynyl, e.g. ethynyl or propargyl. The term "lower" referred to above and hereinafter in connection with organic radicals or compounds respectively, defines such with up to 7, preferably up to 4, carbon atoms. $R_3$ also represents higher alkyl, especially such with 8 to 12 carbon atoms, such as n- or i-octyl, -nonyl, -decyl, -undecyl or -dodecyl.

Said cycloaliphatic or cycloaliphatic-aliphatic radicals R and $R_3$ are preferably 3 to 7 ring-membered cycloalkyl, cycloalkenyl or (cycloalkyl or cycloalkenyl)-lower alkyl groups, e.g. cyclopropyl, cyclobutyl, cyclopentyl or cyclohexyl; cyclopent-1-enyl or cyclohex-1 or 3-enyl; cyclopropylmethyl, cyclobutylmethyl, 1- or 2-cyclopentylethyl; cyclopent-3-enylmethyl or cyclohex-1-enylmethyl.

Said araliphatic radicals R or $R_3$ are preferably isocyclic, or heterocyclic, monocyclic radicals of aromatic character substituting one of said aliphatic groups, preferably a lower alkyl group, either directly or via a linking oxygen or sulfur atom, such as (phenyl, phenoxy, furyl or thienyl)-lower alkyl, unsubstituted or substituted in the aromatic ring, preferably the phenyl ring, by one or more than one, especially one or two, of the same or different substituents, such as lower alkyl, e.g. methyl, ethyl, n- or i-propyl or -butyl; lower alkoxy, e.g. methoxy, ethoxy, n- or i-propoxy or -butoxy; lower alkylenedioxy, e.g. methylenedioxy, 1,1- or 1,2-ethylenedioxy; halogeno, e.g. fluoro, chloro, bromo or iodo; trifluoromethyl; nitro or amino, such as di-lower alkylamino, e.g. dimethylamino or diethylamino. Said aliphatic radicals, especially lower alkyl groups $R_3$, can also be substituted by one of said lower alkoxy groups or one, or up to the maximum number of halogen atoms, as is the case in trifluoromethyl, 2-(methoxy, ethoxy, chloro, bromo or iodo)-ethyl, -propyl or -butyl, 2,2-dichloro-ethyl, -propyl or -butyl, 2,2,2-trichloroethyl, 3-(methoxy, ethoxy, chloro or bromo)-propyl or -butyl, 4-(methoxy or chloro)-butyl.

The compounds of the invention exhibit valuable, prostaglandin-like properties, especially smooth muscle contracting and hypotensive activity. This can be demonstrated either in vitro or in vivo tests, using advantageously mammals, such as mice, rats, guinea pigs or dogs as test objects, or isolated organs thereof. The in vitro tests are performed with the guinea pig ileum in a standard organ bath, e.g. physiological saline. The compounds of the invention, when added to said bath in such amounts to reach concentrations down to about $10^{-8}$ molar, contract the isolated ileum. Histamine hydrochloride and prostaglandin $E_1$ are used as a positive standard and the usual experiments include the control for vehicle and buffer effects.

Moreover, anti-fertility effects are tested in rats or hamsters, e.g. by administering the compounds of the invention to pregnant hamsters, for example 2.5 to 10 mg/kg thereof, subcutaneously once on day five of pregnancy, and inspecting on the eleventh day the uterus thereof for implantation sites and surviving embryos. Also smaller doses can be used for intravenous or intrauterine administration, or larger amounts for oral administration, e.g. to spontaneous hypertensive rats, whose blood pressure is monitored by standard means, and is reduced by said compounds.

Accordingly, the compounds of the invention can be applied enterally or parenterally, e.g. by inhalation of a nebulized aqueous solution, or by peroral, subcutaneous, intramuscular, intraveneous or intrauterine administration, in the dosage range known for the natural prostaglandins. According to the test results obtained, they are useful hypotensive, abortifacient, and luteolytic agents, for example, in the treatment or management of hypertention, especially fertility. They are also valuable intermediates of other preparations, preferably of pharmacologically useful products.

Preferred compounds of the invention are those of Formula I, in which each of R and $R_3$ is lower alkyl, lower alkenyl, lower alkynyl, (3 to 7 ring-membered cycloalkyl or cycloalkenyl)—$C_mH_{2m}$ wherein $m$ is an integer from 0 to 4, (Ph, PhO or Hc)—$C_nH_{2n}$, wherein Ph is phenyl, (lower alkyl)-phenyl, (lower alkoxy)-phenyl, (lower alkylenedioxy)-phenyl, (halogeno)-phenyl, (trifluoromethyl)phenyl, (nitro)-phenyl or (di-lower alkylamino)-phenyl, Hc is furyl or thienyl and $n$ is an integer from 1 to 4, R is also hydrogen, an alkali metal or one equivalent of an alkaline earth metal and $R_3$ is also (lower alkoxy or halo)-lower alkyl, A is ethylene or ethenylene, $R_1$ and $R_2$ are hydrogen or lower alkyl; or the 1,2-dihydro-derivatives thereof.

The highest degree of activity and stability is exhibited by compounds of Formula II

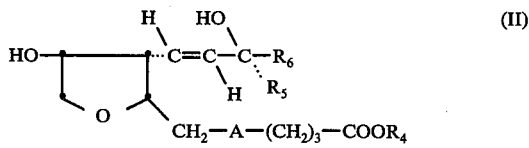

wherein $R_4$ is hydrogen, sodium, potassium or alkyl with up to 4 carbon atoms, A is ethylene or cis-ethenylene, $R_5$ is hydrogen or methyl and $R_6$ is n-(pentyl, pent-2-enyl, hexyl or heptyl), (cyclopropyl, cyclopentyl, cyclohexyl, Ph', Ph'O or 2-furyl)-methyl or -ethyl, wherein Ph' is phenyl, tolyl, anisyl, fluorophenyl, chlorophenyl or trifluoromethylphenyl, or their 4α-hydroxy-isomers.

Of compounds of Formula II, it is advantageous to select those wherein $R_4$ is hydrogen, sodium or potassium, A is ethylene or cis-ethenylene, $R_5$ is hydrogen or methyl and $R_6$ is n-pentyl, n-hexyl, 2-o-fluorophenethyl or m-trifluorophenoxy-methyl, due to their outstanding abortifacient activity and stability.

The compounds of the invention are prepared according to methods known per se, for example by:

(a) reducing in a corresponding 7-[3α-(3-oxo-3-hydrocarbylpropyl or 1-propen- or ynyl)-4-hydroxy-tetrahydro-2β-furyl]-heptan- or 5-enoic acid, or a functional acid- or hydroxy-derivative thereof, the oxo group to hydroxy or (b) oxidizing a corresponding 7-[3α-3-hydroxy-3-hydrocarbylpropyl or 1-propen- or ynyl)-4-hydroxy-tetrahydro-2β-furyl]-heptanal or 5-heptenal, or a functional hydroxy-derivative thereof, to the acid or (c) reacting the 2β-(6-carboxyhexyl or 2-enyl)-4-hydroxy-tetrahydro-3α-furfural, or a functional acid- or hydroxy-derivative thereof, with the ylid of Formula III

wherein X is lower alkyl or phenyl and Y is metallized or etherified hydroxy, or (d) reacting a corresponding [3α-(3-hydroxy-3-hydrocarbylpropyl orlpropen- or ynyl)-4-hydroxy-tetrahydro-2β-furyl]-acetaldehyde or a functional hydroxy derivative thereof, with the compound of Formula IV

wherein X has the above meaning and Z is functionally converted carboxy, and hydrolyzing any resulting hydroxy derivative in basic or acidic media or any resulting acid amide or nitrile in strong basic media and, if desired, esterifying or salifying any resulting acid or hydrolyzing esters or salts or hydrogenating any resulting dehydro derivative until the desired amount of hydrogen is consumed.

A metallized compound III is preferably derived from an alkali metal, e.g. sodium or potassium, and in a corresponding ether Y is preferably tetrahydropyranyloxy or methoxymethoxy. A functional acid derivative used in the above reactions is preferably a metal salt or an ester, e.g. such mentioned above for the compounds of Formula I, or advantageously the nitrile. A functional hydroxy derivative is either an ester or ether, such as a lower alkanoic acid ester, e.g. the acetate or propionate, but advantageously the 2-tetrahydropyranyl ether.

The reduction according to item a) is advantageously carried out with simple or complex light metal hydrides, such as borohydrides or alkali metal or zinc boron- or aluminum-hydrides or lower alkoxyhydrides, e.g. lithium aluminumhydride, sodium or zinc borohydride: lithium tri-t-butoxyaluminumhydride or triethoxyaluminumhydride, or according to Meerwein-Ponndorf-Verley with aluminum lower alkoxides, e.g. the ethoxide or the isopropoxide, preferably in the presence of a lower alkanol, e.g. isopropanol and/or a dihaloaluminum lower alkoxide, e.g. dichloroaluminum isopropoxide.

The oxidation according to (b) is carried out in the conventional manner for oxidizing aldehydes, e.g. with catalytically activated or nascent oxygen, the latter is preferably derived from oxidizing acids or suitable salts or anhydrides thereof, e.g. periodic acid, sodium hypochlorite, chromic, ferric or cupric halides or sulfates, manganese IV, chromium VI, vanadium V, mercuric or silver oxide, in acidic or alkaline media. Said agents are used in the equivalent amounts and/or under careful condition, in order to prevent oxidations at other sites of the molecule.

The reactions according to items (c) and (d) are carried out according to the Wittig Reaction, i.e. either with the isolated reactants of Formulae III or IV, or the precursors thereof, e.g. by combining the corresponding phosphonium halide with a strong base, such as an alkali metal hydroxide, alkoxide, alkyl or phenyl compound first, whereupon the aldehyde is added. Reaction (c) is followed by acid hydrolysis in order to eliminate Y.

Any resulting hydroxy or carboxy derivative is hydrolyzed in the usual manner, for example a lower alkanoic acid ester of the 3β-hydroxy compound, or the nitrile or a lower alkyl ester of the heptanoic acid, with a base, such as an aqueous alkali metal hydroxide or carbonate, or an ether of the 3β-hydroxy compound with an acid, such as a mineral, e.g. hydrohalic or sulfuric acid. Any resulting acid may be esterified or salified in the usual manner, for example, with lower alkanols in the presence of mineral acids, preferably with lower diazoalkanes, or corresponding bases or ion exchangers respectively. Any resulting dehydro derivative (e.g. A = ethenylene) can be selectively hydrogenated by the careful addition of diimine or sufficient hydrogen in the presence of a hydrogenation catalyst, such as platinum, palladium or nickel catalyst. Said hydrogenation is preferably carried out prior to said hydrolysis of the 3β-hydroxy derivatives, in order to protect the prop-1-enyl double bond.

The starting material used can be prepared according to the following formula scheme illustrated by the examples herein:

starting materials for (c) and those of Formula XI such for (d). In case $R_4$ in X contains said group convertible into CHO, such compound is reduced as in a) and CHO

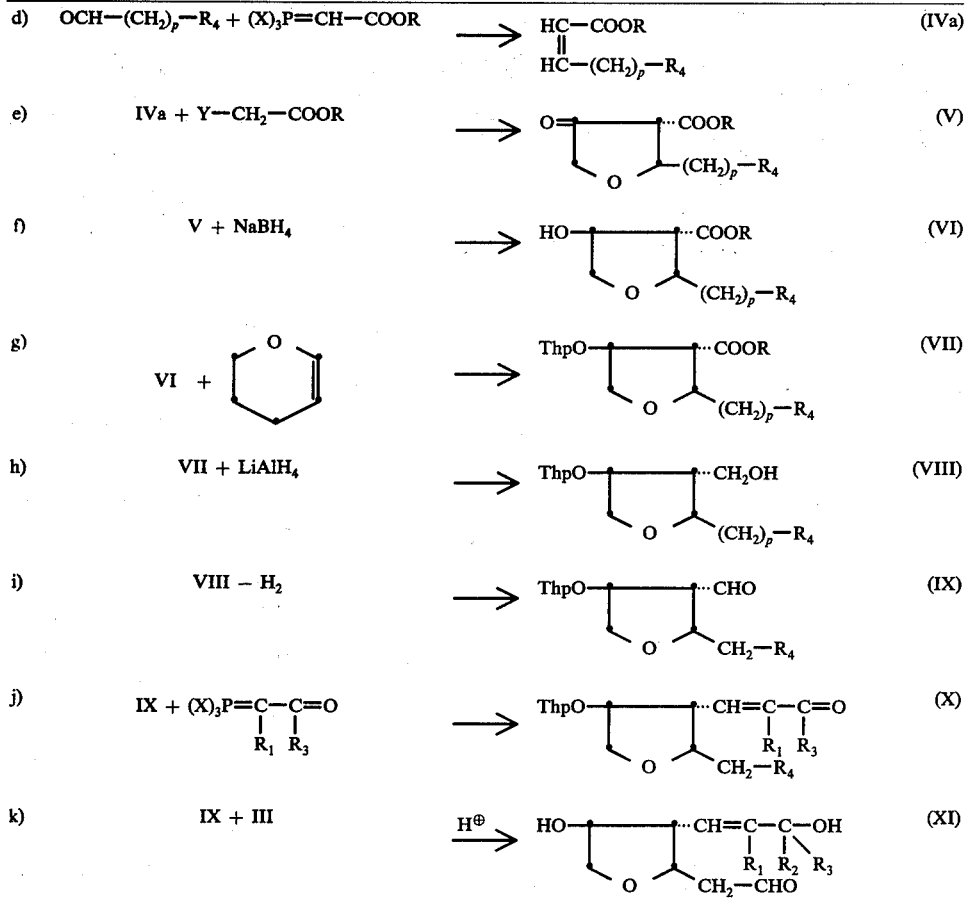

wherein $R_4$ is either $A-(CH_2)_3-CN$ or a group capable of being converted into CHO, such as an etherified dihydroxymethyl(acetal) group, derived, for example, from lower alkanols or glycols, e.g. methanol, ethanol or ethylene glycol and $p$ is the integer 0 or 1. Accordingly, in case $R_4$ is $A-(CH_2)_3$-CN, compounds of Formula X are starting materials for the reduction mentioned under item a), compounds of Formula IX are is liberated in acids, starting material for (b) is obtained. Said products can be converted into the other starting materials as described above for the resulting compounds of Formula I.

Another method for the preparation of the starting materials mentioned under item (a) to (c) is the following:

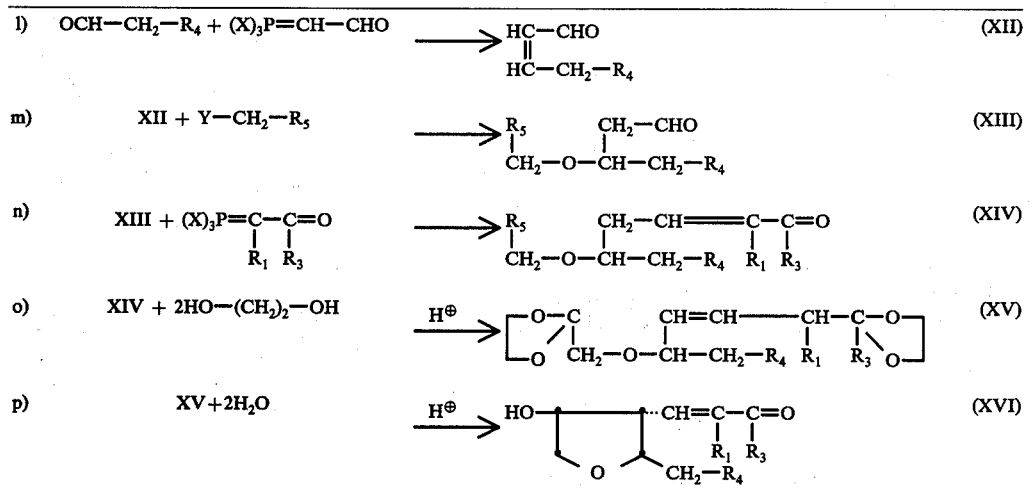

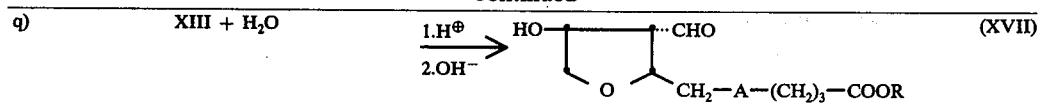

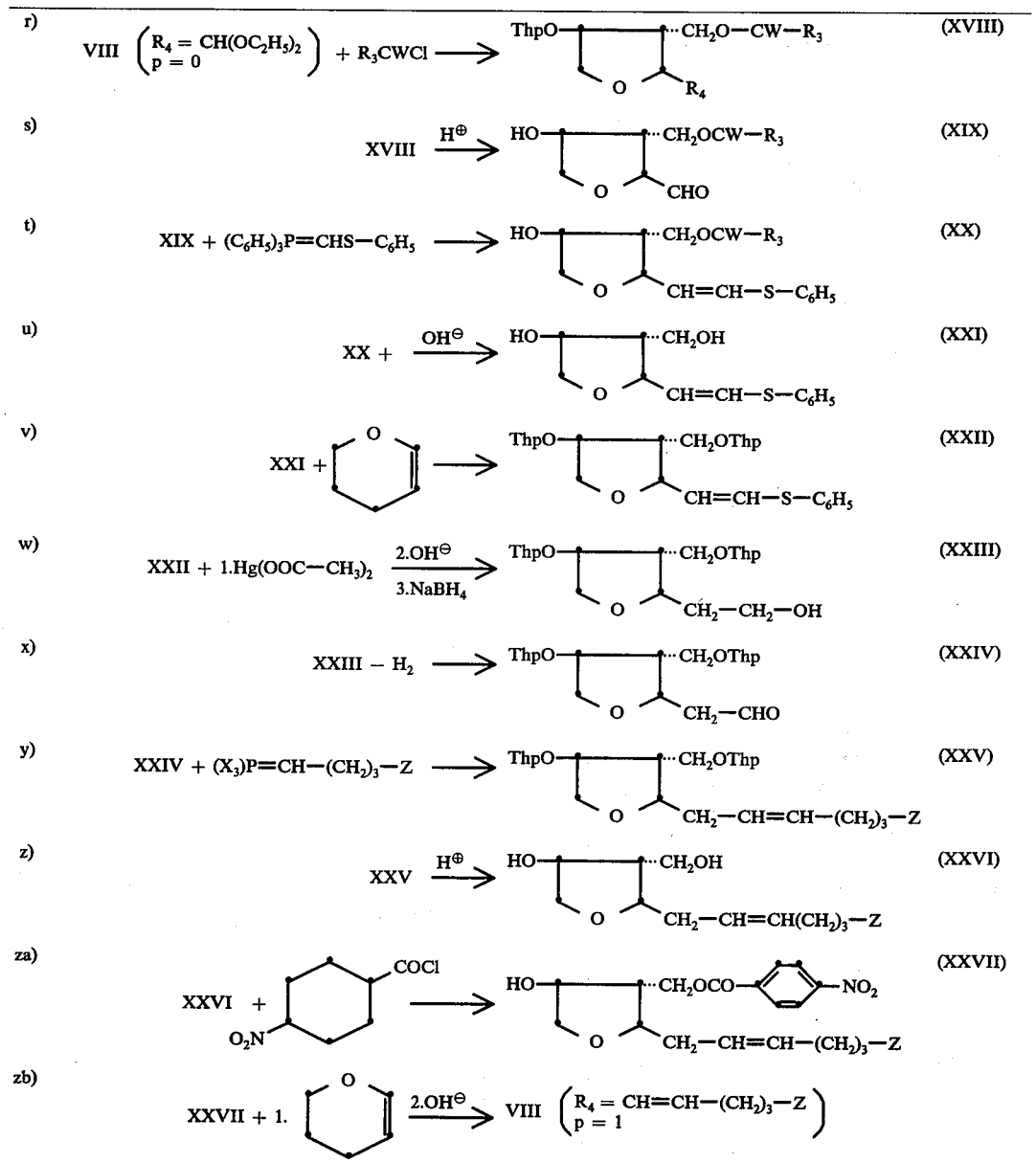

wherein $R_5$ is said group capable of being converted into CHO and the other symbols have the meanings given above. Accordingly, compounds of Formula XVI are starting materials for a) and XVII for b) if $R_4$ is whereupon CHO is liberated in acidic media, starting material for d) is obtained.

Another process for said starting material is depicted by the following scheme:

A—$(CH_2)_3$-CN. In case $R_4$ in Formulae X and XVI is said group capable or being converted into CHO and such compound is reacted as in (c) or reduced as in (a), wherein W is $H_2$ or O. The latter VIII is converted to the corresponding X as shown above.

Finally, selected compounds of the invention, or starting materials, can be prepared as follows:

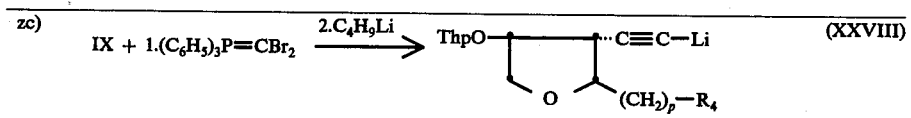

zd) 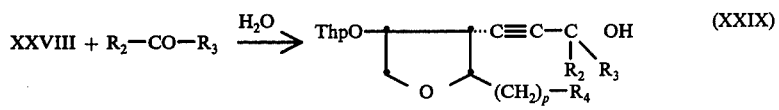 (XXIX)

ze) 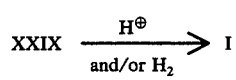 I

The above steps (*d*), (*j*), (*k*), (*l*), (*n*), (*s*), (*t*), (*u*), (*x*), (*y*) and (*z*) are carried out analogous to b) or c); the condensations according to (*e*) or (*m*) advantageously in di-lower alkylsulfoxides, e.g. dimethylsulfoxide, followed by acid treatment; the reductions according to (*f*), (*h*) and (*w*) are performed analogously to (*a*); the etherifications, ketalizations or trans-ketalizations according to (*g*), (*o*), (*v*) or (*zb*) respectively are advantageously carried out in the presence of an organic acid, e.g. picric or p-toluenesulfonic acid and an inert diluent, such as a halogenalkane, e.g. methylene chloride; the oxidation according to (*i*) or (*x*) is advantageously performed with the use of heavy metal oxides, e.g. silver or chromium VI oxide, advantageously in inert solvents, such as halogenalkanes and/or pyridine. The ring-closure according to (*p*) occurs spontaneously after acid hydrolysis of the bis-ketal, whereas that according to (*q*) requires first acid hydrolysis to convert $R_5$ to formyl and the following aldol condensation occurs under basic conditions, e.g. in the presence of alkali metals, their alkoxides or amides. The esterification or benzylation according to (*v*) and (*za*) are carried out in the usual manner, preferably in the presence of a base, e.g. pyridine, or sodium hydride respectively.

Resulting mixtures of isomers can be separated into the single isomers by methods in themselves known, e.g. by fractional distillation, crystallization and/or chromatography. Racemic products can likewise be resolved into the optical antipodes, for example, by separation of diastereomeric esters or salts thereof, e.g. by the fractional crystallization of d- or ρ-2-pyrrolidone-3-carboxylates, -3β-acetoxy-Δ⁵-etienates, -α-(2,4,5,7-tetranitro-9-fluorenylideneaminooxy)-propionates or salts of d- or ρ-α-phenethylamine, -1-phenyl-2-propylamine or -dihydroabieylamine.

The above reactions are carried out according to standard methods, in the presence or absence of diluents, preferably such as are inert to the reagents and are solvents thereof, of catalysts, condensing, neutralizing agents and/or inert atmospheres, at low temperatures, room temperature or elevated temperatures, at atmospheric or superatmospheric pressure. For example, any generated mineral or sulfonic acid may be neutralized with inorganic or organic bases, such as alkali or alkaline earth metal hydroxides, carbonates or bicarbonates, or nitrogen bases, such as tri-lower alkylamines or pyridine.

The invention also comprises any modification of the above process, wherein a compound resulting as an intermediate at any stage thereof, is used as starting material and the remaining steps are carried out or the process is discontinued at any stage thereof, or in which the starting material is formed under the reaction conditions or is used in the form of its salts or other derivatives. In the above processes, those starting materials are advantageously selected, which yield the above-described preferred embodiments of the invention.

The pharmacologically active compounds of the invention are useful in the manufacture of pharmaceutical compositions containing an effective amount thereof in conjunction or admixture with excipients suitable for either enteral or parenteral application. Preferred are tablets and gelatin capsules comprising the active ingredient together with a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, d) disintegrants, e.g. starches, agar, alginic acid or its sodium salt, enzymes of the binders or effervescent mixtures and/or e) adsorbents, colorants, flavors, sweeteners and coating agents, e.g. concentrated aqueous sugar solutions containing gum arabic, talcum and/or titanium dioxide, or solutions of lacquers in easily volatile organic solvents, in order to obtain regular or sustained release formulations. Injectable compositions are preferably aqueous isotonic solutions or suspensions, and suppositories are advantageously fatty emulsions or suspensions, e.g. in cocoa butter. They may be sterilized and/or contain adjuvants, such as preserving, stabilizing, wetting or emulsifying agents, solution promoters, salts for regulating the osmotic pressure and/or buffers. They may also contain other therapeutic agents, e.g. diuretics and/or psychotherapeutics as in U.S. Pat. Nos. 3,081,230 or 3,499,082. Said compositions are prepared according to conventional mixing, granulating or coating methods respectively and contain about 0.001 to 75%, preferably about 1 to 50% of the active ingredient.

The following examples are intended to illustrate the invention and are not to be construed as being limitations thereon. Temperatures are given in degrees Centigrade, and all parts wherever given are parts by weight. If not otherwise stated, all evaporations are carried out under reduced pressure, the infrared spectra are obtained from about 1–5% solutions in chloroform and the N.M.R. spectra from about 10% solutions in deuterochloroform at 60 Mc/sec. with tetramethylsilane as zero.

EXAMPLE 1

To the solution of 0.7 g of 7-[3α-(3-oxo-1-trans-octenyl)-4β-(2-tetrahydropyranyloxy)-tetrahydro-2β-furyl]-heptanoic acid nitrile in 15 ml of ethanol, 0.7 g of sodium borohydride are added while stirring at 0°. After ½ hour, the mixture is poured into ice water, extracted with diethyl ether, the extract washed with water and saturated aqueous sodium chloride, dried and evaporated, to yield the 7-[3α-(3ξ-hydroxy-1-trans-octenyl)-4β-(2-tetrahydropyranyloxy)-tetrahydro-2β-furyl]-heptanoic acid nitrile of the formula

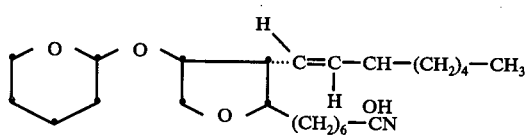

showing in the I.R. spectrum bands at 3500 and 2253, but none at 1690 or 1630 cm$^{-1}$.

To the solution of 0.7 g thereof in 15 ml of methanol, 0.1 ml 2N sulfuric acid are added and the mixture allowed to stand at room temperature overnight. It is evaporated, the residue taken up in water, the mixture extracted with diethyl ether, the extract washed with water and saturated aqueous sodium chloride, dried and evaporated. The residue is subjected to preparative thin-layer chromatography on silica gel plates (1 mm thick), eluted twice with ethyl acetate-methylene chloride (4:1) and of the two main fractions, the slower moving isomer is isolated, to yield the 7-[3α-(3β-hydroxy-1-trans-octenyl)-4β-hydroxy-tetrahydro-2β-furyl]-heptanoic acid nitrile of the formula

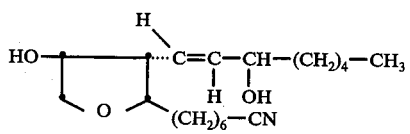

showing in the N.M.R. spectrum peaks at 5.65, 1.42 and 0.90 ppm.

The mixture of 0.15 g thereof, 3 ml of methanol, 0.5 ml of water and 0.5 ml of 20% aqueous potassium hydroxide is heated in a sealed tube to 115°–120° for 48 hours and evaporated. The residue is taken up in 10 ml of water and 10 ml of saturated aqueous sodium chloride, the mixture neutralized with dry ice and extracted 8 times with diethyl ether. The extract is dried and evaporated, to yield the 7-[3α-(3β-hydroxy-1-trans-octenyl)-4β-hydroxy-tetrahydro-2β-furyl]-heptanoic acid of the formula

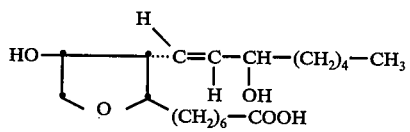

showing in the mass spectrum fragments of 324, 308, 255 and 215 m/e.

The starting material is prepared as follows: The mixture of 14 g of 7-cyanoheptanal, 38 g of ethyl triphenylphosphoranylidene-acetate and 100 ml of benzene is refluxed for 15 hours and evaporated. The residue is triturated with diethyl ether, filtered and the filtrate evaporated. The residue is allowed to stand overnight in the refrigerator, triturated with the minimum amount of diethyl ether, the suspension filtered, the filtrate evaporated, the residue distilled and the fraction boiling at 130°–138°/0.1 mm Hg collected, to yield the 9-cyano-2-nonenoic acid ethyl ester of the formula

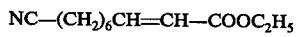

33.4 g thereof are added at once at 10° to the mixture prepared from 3.68 g of pulverized sodium and 16.9 g of ethyl glycolate in 300 ml of diethyl ether, evaporating the mixture after stirring it at room temperature overnight and adding 150 ml of dimethylsulfoxide. The mixture is stirred at room temperature for 2 hours, poured into 100 ml of cold 2N hydrochloric acid and extracted with diethyl ether. The extract is washed with water, dried and evaporated, to yield the 2-(6-cyanohexyl)-4-oxo-tetrahydrofuran-3-carboxylic acid ethyl ester of the formula

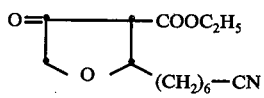

which is used as such without further purification.

To the solution of 37.1 g thereof in 360 ml of ethanol, 3.6 g of sodium borohydride are added during 5 minutes while stirring at 0°. After one half hour, the mixture is poured onto ice water, extracted with diethyl ether, the extract washed with water and saturated aqueous sodium chloride, dried and evaporated. Each gram of residue is chromatographed on 30 g of silica gel and the column eluted with ethyl acetate-methylene chloride (1:1), to yield the 2-(6-cyanohexyl)-4-hydroxy-tetrahydrofuran-3-carboxylic acid ethyl ester of the formula

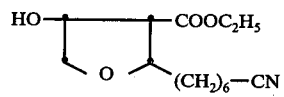

showing in the I.R. spectrum bands at 3500, 2250 and 1730 cm$^{-1}$.

The mixture of 594 mg thereof, 450 mg of dihydropyrane, 30 mg of picric acid and 10 ml of methylene chloride is allowed to stand at room temperature overnight. It is evaporated, the residue taken up in diethyl ether, the solution washed three times with 10% aqueous potassium bicarbonate, once with water and saturated aqueous sodium chloride, dried and evaporated, to yield the 2-(6-cyanohexyl-4-(2-tetrahydropyranyloxy)-tetrahydrofuran-3-carboxylic acid ethyl ester of the formula

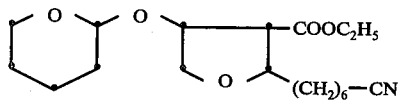

showing in the I.R. spectrum bands at 2250, 1730 and none at 3500 cm$^{-1}$.

To the solution of 735 mg thereof in 35 ml of tetrahydrofuran, 100 ml of lithium aluminum hydride are added while stirring at −20°. After 3 hours, 35 ml of diethyl ether are added, followed by a few drops of methanol and water. It is filtered, the filtrate evaporated, the residue chromatographed on 30 g of silica gel and eluted with ethyl acetate-methylene chloride (1:9), to yield the 7-[3-hydroxymethyl-4-(2-tetrahydropyranyloxy)-tetrahydro-2-furyl]-heptanoic acid nitrile of the formula

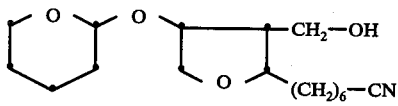

showing in the I.R. spectrum bands at 3500, 2930, 2855 and none at 1730 cm$^{-1}$.

To the solution of 1.72 g thereof in 500 ml of methylene chloride, the solution of 10 g of pyridine-chromium trioxide complex in 300 ml of methylene chloride is added at once and the mixture stirred at room temperature for 15 minutes. It is washed with water, dried, treated with charcoal, filtered and evaporated, to yield the 2-(6-cyanohexyl)-4-(2-tetrahydropyranyloxy)-tetrahydrofurane-3-carboxaldehyde of the formula

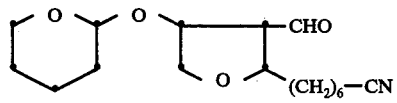

showing in the I.R. spectrum bands at 2725, 2250 and 1735 cm$^{-1}$.

To the solution of 1.4 g thereof in 20 ml of diethyl ether, 2 g of 1-tri-n-butylphosphoranilidene-2-heptanone are added while stirring and the mixture allowed to stand at room temperature overnight. It is evaporated, the residue subjected to preparative thin-layer chromatography on silica gel plates (1 mm thick), twice eluted with ethyl acetate-methylene chloride (1:4), to yield the 7-[3α-(3-oxo-1-trans-octenyl)-4β-(2-tetrahydropyranyloxy)-tetrahydro-2β-furyl]-heptanoic acid nitrile of the formula

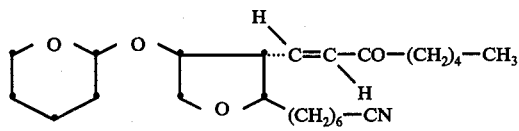

having Rf = 0.55.

The corresponding 4α-tetrahydropyranyloxy epimer has Rf = 0.38.

To the solution of 1 mg of the 4β-epimer in 10 ml of methanol, 50 μl of 2N-sulfuric acid are added and the mixture allowed to stand overnight at room temperature. It is evaporated, the residue taken up in diethyl ether, the solution washed with water, dried and evaporated. The residue is subjected to preparative thin-layer chromatography as before and twice eluted with ethyl acetate-methylene chloride (1:1), to yield the 7-[3α-(3-oxo-1-trans-octenyl)-4β-hydroxy-tetrahydro-2β-furyl]-heptanoic acid nitrile of the formula

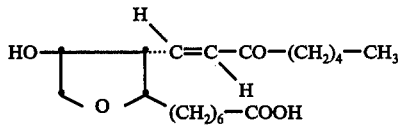

showing in the N.M.R. spectrum peaks at 6.68, 6.18 and 4.27 ppm. It can be reduced analogous to its 2-tetrahydropyranyl ether, to yield the 7-[3α-(3β-hydroxy-1-trans-octenyl)-4β-hydroxy-tetrahydro-2β-furyl]-heptanoic acid nitrile directly.

EXAMPLE 2

According to the methods shown in Example 1, the 7-[3α-(3-oxo-1-trans-octenyl)-4α-(2-tetrahydropyranyloxy)-tetrahydro-2β-furyl]-heptanoic acid nitrile (Rf = 0.38) is either hydrolyzed to the 4α-alcohol, showing in the N.M.R. spectrum peaks at 6.87, 4.40 and 0.90 ppm, either compound reduced with sodium borohydride and the resulting ether hydrolyzed, to yield the 7-[3α-(3ξ-hydroxy-1-trans-octenyl)-4α-hydroxy-tetrahydro-2β-furyl]-heptanoic acid nitrile of the formula

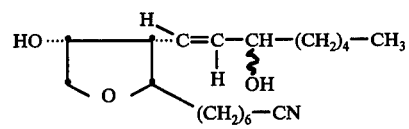

It is chromatographed on silica gel and eluted with ethyl acetate-methylene chloride (4:1) to yield the 3α, 4α-dihydroxy diastereomer as the slower moving fraction melting at 63°-64°.

It is analogously hydrolyzed to the 7-[3α-(3α-hydroxy-1-trans-octenyl)-4α-hydroxy-tetrahydro-2β-furyl]-heptanoic acid melting at 52°-54°.

EXAMPLE 3

To the solution of 50 mg of 7-[3α-(5-ethoxy-3-oxo-1-trans-pentenyl)-4ξ-(2-tetrahydropyranyloxy)-tetrahydro-2β-furyl]-heptanoic acid methyl ester in 8 ml of ethanol, 50 mg of sodium borohydride are added and the mixture stirred for ½ hour at room temperature. It is diluted with 50 ml of diethyl ether, washed with water and saturated aqueous sodium chloride, dried and evaporated. The residue is chromatographed on silica gel and eluted with benzene-ethyl acetate-cyclohexane-methanol (10:10:4:1), to yield the 7-[3α-(5-ethoxy-3ξ-hydroxy-1-trans-pentenyl)-4ξ-(2-tetrahydropyranyloxy)-tetrahydro-2β-furyl]-heptanoic acid methyl ester of the formula

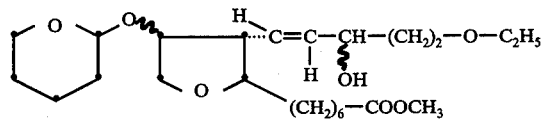

having Rf = 0.38 and showing in the I.R. spectrum bands at 3480, 2940 and 1725 cm$^{-1}$.

To the solution of 41 mg thereof in 7 ml of methanol 50 μl of 2N sulfuric acid are added and the mixture allowed to stand for 10 hours at room temperature. It is diluted with 50 ml of diethyl ether, washed with water and saturated aqueous sodium chloride, dried and evaporated. The residue is chromatographed on silica gel and eluted with benzene-ethyl acetate-cyclohexanemethanol (4:4:1:1), to yield the 7-[3α-(5-ethoxy-3ξ-hydroxy-1-trans-pentenyl)-4ξ-hydroxy-tetrahydro-2β-furyl]-heptanoic acid methyl ester having Rf = 0.44 and showing in the N.M.R. spectrum peaks at 5.70, 3.67, 2.30 and 1.40 ppm.

The mixture of 35 mg thereof, 7 ml of methanol and 0.7 ml of 10% aqueous potassium carbonate is allowed to stand at room temperature for 48 hours and evaporated. The residue is taken up in 5 ml of water, 5 ml of saturated aqueous sodium chloride are added and the mixture is washed with diethyl ether. It is acidified with 2N sulfuric acid, extracted with diethyl ether, the extract dried and evaporated. The residue is chromatographed on silica gel and eluted with benzene-ethyl acetate-cyclohexanemethanol-formic acid (4:4:1:1:0.04), to yield the 7-(3α-(5-ethoxy-3ξ-hydroxy-1-trans-pentenyl)-4ξ-hydroxy-tetrahydro-2β-furyl]-heptanoic acid of the formula

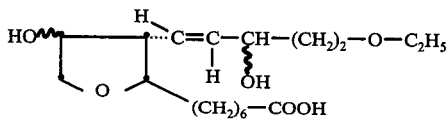

having Rf = 0.31 and showing in the mass spectrum fragments of 326, 295, 280, 168, 141 and 101 m/e.

The starting material is prepared as follows: The mixture of 1.65 g of 7-[3-hydroxymethyl-4-(2-tetrahydropyranyloxy)-tetrahydro-2-furyl]-heptanoic acid nitrile, 24 ml of methanol, 8 ml of water and 6 ml of 20% aqueous potassium hydroxide is heated in a sealed tube to 110° for 48 hours. It is evaporated, the residue taken up in 10 ml of water and 10 ml of saturated aqueous sodium chloride, the mixture washed with diethyl ether and the aqueous layer acidified with dry ice to pH = 5. It is extracted 8 times with diethyl ether, the extract dried, concentrated and the concentrate treated with ethereal diazomethane until the yellow color persists. After a half hour stirring at room temperature the mixture is evaporated, the residue chromatographed on silica gel and eluted with ethyl acetate-methylene chloride (1:1), to yield the 7-[3α-hydroxymethyl-4ξ-(2-tetrahydropyranyloxy)-tetrahydro-2β-furyl]-heptanoic acid methyl ester having Rf = 0.36.

To the solution of 100 mg thereof in 50 ml of methylene chloride, the mixture of 450 mg of pyridine-chromium trioxide complex and 30 ml of methylene chloride is added at once while stirring at room temperature for 10 minutes. The mixture is washed with water, dried, decolorized with charcoal, evaporated, the residue chromatographed on silica gel and eluted with ethyl acetate-methylene chloride (2.5:22.5), to yield the 2β-(6-methoxycarbonylhexyl)-4ξ-(2-tetrahydropyranyloxy)-tetrahydrofuran-3α-carboxaldehyde having Rf = 0.29.

The mixture of 89 mg thereof, 110 mg of 1-tri-n-butyl-phosphoranylidene-4-ethoxy-2-butanone and 5 ml of diethyl ether is allowed to stand at room temperature overnight. It is evaporated, the residue chromatographed on silica gel and eluted with benzenecyclohexane-ethyl acetate (2:1:2), to yield the 7-[3α-(5-ethoxy-3-oxo-1-trans-pentenyl)-4ξ-(2-tetrahydropyranyloxy)-tetrahydro-2β-furyl]-heptanoic acid methyl ester having Rf = 0.36.

EXAMPLE 4

To the solution of 0.25 g of 7-[3α-(3-oxo-1-trans-octenyl-4β-(2-tetrahydropyranyloxy)-tetrahydro-2β-furyl]-5-cis-heptenoic acid methyl ester in 5 ml of ethanol, 50 mg of sodium borohydride are added while stirring at 0°. After ½ hour the mixture is diluted with diethyl ether, washed with water, dried and evaporated. The residue is chromatographed on silica gel and the column eluted with ethyl acetate-methylene chloride (1:4), to yield the 7-[3α-(3ξ-hydroxy-1-trans-octenyl)-4β-(2-tetrahydropyranyloxy)-tetrahydro-2β-furyl]-5-cis-heptenoic acid methyl ester of the formula

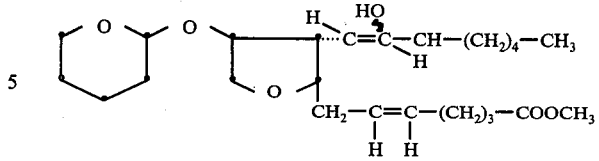

having an Rf = 0.295.

The mixture of 0.24 g thereof, 2 ml of methanol and 15 mg of p-toluenesulfonic acid is stirred at room temperature overnight. It is combined with 20 μl of triethylamine, evaporated under reduced pressure and the residue taken up in diethyl ether. The solution is dried, evaporated and the residue subjected to preparative thin-layer chromatography on silica gel plates (1 mm thick), eluted twice with ethyl acetate-methylene chloride (1:1) and the fraction corresponding to Rf = 0.218 yields the 7-[3α-(3β-hydroxy-1-trans-octenyl)-4β-hydroxy-tetrahydro-2β-furyl]-5-cis-heptenoic acid methyl ester of the formula

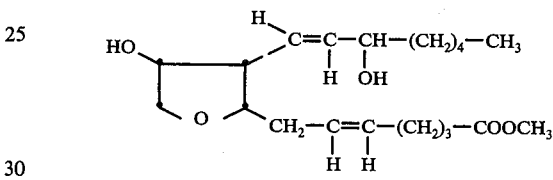

(The 3α-hydroxy-epimer thereof has an Rf = 0.335).

The mixture of 82 mg thereof, 2 ml of methanol and 3 ml of 0.1 N aqueous sodium hydroxide is stirred at room temperature for 5 hours and evaporated. The residue is dissolved in 5 ml of saturated aqueous sodium chloride and 5 ml of water and extracted with diethyl ether. The aqueous layer is neutralized with 3 ml of 0.1 N aqueous hydrochloric acid and extracted three times with diethyl ether. The extract is dried and evaporated, to yield the 7-[3α-(3β-hydroxy-1-trans-octenyl)-4β-hydroxy-tetrahydro-2β-furyl]-5-cis-heptenoic acid of the formula

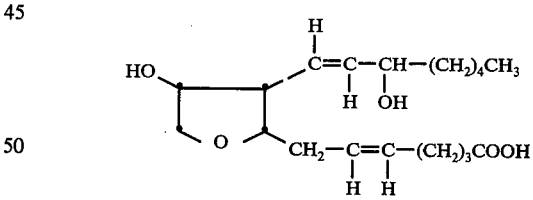

having an Rf = 0.573 (silica gel, benzene-dioxane-acetic acid, 10:10:0.5). The corresponding 3α-hydroxy-epimer has an Rf = 0.654.

The starting material is prepared as follows:

The mixture of 10.2 g of 2,2-diethoxy acetaldehyde, 27.8 g of methyl triphenylphosphoranylidene-acetate and 130 ml of benzene is refluxed for 15 hours and evaporated. The residue is triturated with diethyl ether, filtered and the filtrate evaporated. The residue is allowed to stand overnight in the refrigerator, triturated with the minimum amount of diethyl ether, the suspension filtered, the filtrate evaporated, the residue distilled and the fraction boiling at 50°-54°/0.1 mm Hg collected, to yield the 4,4-diethoxy-crotonic acid methyl ester.

20.5 g thereof are added at once at 0° to the mixture, prepared from 2.76 g of pulverized sodium and 11.9 g of methyl glycolate in 300 ml of diethyl ether, evaporating the mixture after stirring it at room temperature overnight and adding 110 ml of dimethylsulfoxide and 50 ml of dimethylformamide. The mixture is stirred at 0° for 2 hours and subsequently at room temperature for 1 hour, poured into 100 ml of cold water and extracted once with diethyl ether. The aqueous layer is acidified with 2 N hydrochloric acid and extracted with diethyl ether. The extract is washed with water dried, evaporated, the residue distilled and the fraction boiling at 123°–124°/0.3 mm Hg collected, to yield the 2-diethoxymethyl-4-oxo-tetrahydrofuran-3-carboxylic acid methyl ester of the formula

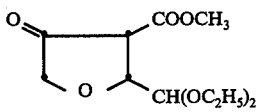

The solution of 22 g thereof in 30 ml of ethanol is added at −70° to the solution of 3.4 g of sodium borohydride in 270 ml of ethanol and 270 ml of tetrahydrofuran over a period of 10 minutes. After ½ hour the mixture is poured onto water and extracted three times with diethyl ether. The extract is washed with water and saturated aqueous sodium chloride, dried and evaporated. Each gram of the residue is chromatographed on 50 g of silica gel and the column eluted with ethyl acetate-methylene chloride (1:4), to yield the less polar 2β-diethoxymethyl-4β-hydroxy-tetrahydrofuran-3α-carboxylic acid methyl ester of the formula

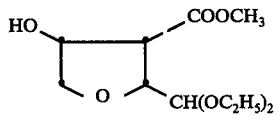

showing in the NMR spectrum bands at 4.61, 4.37, 3.92, 3.75 and 1.25 ppm.

(The more polar 2β-diethoxymethyl-4α-hydroxy-tetrahydrofuran-3α-carboxylic acid methyl ester shows in the NMR spectrum bands at 4.6, 4.0, 3.83 and 1.22 ppm.)

The mixture of 2.02 g of the former isomer, 1.39 g of dihydropyrane, 160 mg of picric acid and 30 ml of methylene chloride is allowed to stand at room temperature overnight. It is evaporated, the residue taken up in diethyl ether, the solution washed three times with 10% aqueous potassium bicarbonate, once with water and saturated aqueous sodium chloride, dried and evaporated, to yield the 2β-diethoxymethyl-4β-(2-tetrahydropyranyloxy)-tetrahydrofuran-3α-carboxylic acid methyl ester showing in the NMR spectrum bands at 4.6, 3.72, 1.63 and 1.22 ppm.

To the solution of 2.7 g thereof in 160 ml of diethyl ether, 314 mg of lithium aluminum hydride are added while stirring at 0° C. After 3 hours 100 ml of diethyl ether are added, followed by a few drops of methanol and water. It is filtered and the filtrate evaporated, to yield the 2β-diethoxymethyl-3α-hydroxymethyl-4β-(2-tetrahydropyranyloxy)-tetrahydrofuran, showing in the NMR spectrum bands at 4.58, 6.66 and 1.29 ppm.

To the solution of 4.87 g thereof in 10 ml of pyridine, 2.05 ml of benzoyl chloride are added over a period of two minutes while stirring at 0°. After one hour, the mixture is diluted with diethyl ether and washed with water, 1 N hydrochloric acid, again with water and brine, dried and evaporated, to yield the 3α-benzoyloxymethyl-2β-diethoxymethyl-4β-(2-tetrahydropyranyloxy)-tetrahydrofuran, showing in the NMR spectrum bands of 8.1, 7.5, 1.6 and 1.25 ppm.

The mixture of 6.4 g thereof, 60 ml of glacial acetic acid and 72 ml of water is heated with stirring at 60° C for 24 hours. It is evaporated under reduced pressure, the residue dissolved in 20 ml of toluene, dried and evaporated, to yield the 3α-benzoyloxymethyl-4β-hydroxy-tetrahydrofuran-2β-carboxaldehyde, showing in the NMR spectrum bands at 8.0, 7.45, 4.25 and 3.91 ppm.

The solution of 4.98 g thereof in 25 ml of dry tetrahydrofuran is added dropwise at 0° to the solution, prepared from adding dropwise 40.8 ml of n-butyl lithium to a stirred suspension of 27.5 g of phenyl-thiomethyltriphenylphosphonium chloride in 500 ml of diethyl ether and allowing the mixture to stir at room temperature for ½ hour. Thereupon it is poured into water, the organic layer dried and evaporated. The residue is triturated with diethyl ether, filtered and evaporated. Each gram of the residue is chromatographed on 30 g of silica gel and the column eluted with ethyl acetate-methylene chloride (1:4), to yield the 3α-benzoyloxymethyl-4β-hydroxy-2β-(2-phenylthioethenyl)-tetrahydrofuran of the formula

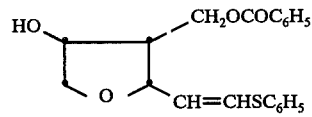

showing in the NMR spectrum bands at 7.98, 7.41, 7.15, 6.37, 5.91, 4.3 and 3.87 ppm.

The mixture of 4.7 g thereof, 50 ml of ethanol and 20 ml of 10% aqueous potassium carbonate is stirred at room temperature for two hours and evaporated. The residue is taken up in diethyl ether, the solution washed with water, dried and evaporated to yield 4β-hydroxy-3α-hydroxymethyl-2β-(2-phenylthioethenyl)-tetrahydrofuran analyzing correctly.

The mixture of 3.22 g thereof, 3.62 ml of dihydropyrane, 50 ml of methylene chloride and 93 mg of picric acid is allowed to stand at room temperature overnight. It is diluted with diethyl ether, washed with 10% aqueous potassium bicarbonate and water, dried and evaporated, to yield the 2β-(2-phenylthioethenyl)-4β-(2-tetrahydropyranyloxy)-3α-(2-tetrahydropyranyloxymethyl)-tetrahydrofuran, showing in the NMR spectrum bands at 7.23, 6.35, 6.27, 4.6 and 1.58 ppm.

The mixture of 5.87 g thereof, 66 ml of glacial acetic acid, 4.5 ml of acetic anhydride and 8.95 g of mercuric acetate is heated with stirring at 50° for 2 hours. It is evaporated under reduced pressure, the residue dissolved in 110 ml of methanol and the solution treated with 37 ml of 10% aqueous potassium carbonate at room temperature for 15 minutes. The mixture is cooled to 0°, and 3 g of sodium borohydride are added with stirring. After two hours, the mixture is evaporated, the residue taken up in diethyl ether, the solution washed with water, dried and evaporated. The residue is subjected to preparative thin layer chromatography on silica gel plates (1 mm thick), eluted with ethyl acetate and the band corresponding to Rf = 0.25 is extracted with ethyl acetatemethanol (1:1), to yield the 2β-(2- hydroxyethyl)-4β-(2-tetrahydropyranyloxy)-3α-(2-tetrahydropyranyloxymethyl)-tetrahydrofuran, showing in the NMR spectrum bands at 4.6, 3.76 and 1.58 ppm.

To the solution of 270 mg thereof in 150 ml of methylene chloride, 1.2 g of chromium trioxide-pyridine complex are added at once at room temperature while stirring. After 10 minutes the mixture is poured into water, the organic layer separated, dried, decolorized with charcoal and evaporated, to yield 2β-[4β-(2-tetrahydropyranyloxy)-3α-(2-tetrahydropyranyloxymethyl)-tetrahydro-2β-furyl]-acetaldehyde, showing in the I.R. spectrum bands at 2930, 2855, 2720 and 1720 cm$^{-1}$.

The solution of 250 mg thereof in 1 ml of dimethylsulfoxide is added dropwise at room temperature with stirring to the mixture, prepared by adding 7.4 ml of 1.5 molar sodium methylsulfinylmethiodide in dimethylsulfoxide to the solution of 1.1 g of 4-carboxybutyl-triphenylphosphonium bromide in 5 ml of dimethylsulfoxide. After 15 minutes the mixture is poured into water and washed once with diethyl ether. The aqueous layer is acidified with dry ice and extracted five times with diethyl ether. The extract is washed with water and saturated aqueous sodium chloride, dried and evaporated. The residue is dissolved in 5 ml of methanol and treated with an excess of ethereal diazomethane at 0° for ½ hour. It is evaporated and the residue subjected to preparative thin layer chromatography on silica gel plates and eluted with ethyl acetate-methylene chloride (1:4), to yield the 7-[4β-(2-tetrahydropyranyloxy)-3α-(2-tetrahydropyranyloxymethyl)-tetrahydro-2β-furyl]-5-cis-heptenoic acid methyl ester.

The mixture of 167 mg thereof, 5 ml of methanol and 10 mg of p-toluenesulfonic acid is allowed to stand at room temperature overnight and evaporated. The residue is taken up in diethyl ether, the solution washed with water, dried and evaporated. The residue is subjected to preparative thin layer chromatography on silica gel plates and eluted with ethyl acetate, to yield the 7-(4β-hydroxy-3α-hydroxymethyl-tetrahydro-2β-furyl)-5-cis-heptenoic acid methyl ester of the formula

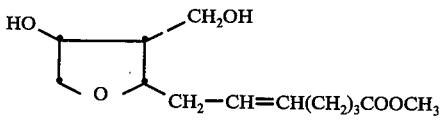

having Rf = 0.235.

To the solution of 534 mg thereof in 5 ml of pyridine is added dropwise at 0° the solution of 386 mg of p-nitrobenzoyl chloride in 5 ml of pyridine while stirring. After three hours stirring at 0°, the mixture is stirred at room temperature overnight, poured into water and extracted with diethyl ether. The extract is washed with 1 N hydrochloric acid and water, dried and evaporated. The residue is subjected to preparative thin layer chromatography on silica gel plates and eluted with ethyl acetate-methylene chloride, (4:1), to yield the 7-(3α-p-nitrobenzoyloxymethyl-4β-hydroxy-tetrahydro-2β-furyl)-5-cis-heptenoic acid methyl ester having Rf = 0.187.

The mixture of 55 mg thereof, 1 ml of methylene chloride, 15 mg of dihydropyrane and 2 mg of picric acid is stirred at room temperature overnight. It is diluted with diethyl ether, washed with 10% aqueous potassium bicarbonate, water, dried and evaporated, to yield the 7-[3α-p-nitrobenzoyloxy-4β-(2-tetrahydropyranyloxy)tetrahydro-2β-furyl]-5-cis-heptenoic acid methyl ester, having Rf = 0.28 on silica gel plates eluted with ethyl acetate-methylene chloride (1:4).

The mixture of 75 mg thereof, 1 ml of methanol and 0.2 ml of 10% aqueous potassium carbonate is stirred at room temperature for 10 minutes, diluted with 25 ml of diethyl ether, washed with water and saturated aqueous sodium chloride, dried and evaporated, to yield the 7-[3α-hydroxymethyl-4β-(2-tetrahydropyranyloxy)-tetrahydro-2β-furyl]-5-cis-heptenoic acid methyl ester, having an Rf = 0.143 on silica gel plates eluted with ethyl acetate-methylene chloride (1:4).

To the solution of 60 mg thereof in 30 ml of methylene chloride, 270 mg of pyridine-chromium trioxide complex is added at once and the mixture stirred at room temperature for 15 minutes. It is washed with water, dried, treated with charcoal, filtered and evaporated, to yield the 7-(3α-formyl-4β-(2-tetrahydropyranyloxy)tetrahydro-2β-furyl)-5-cis-heptenoic acid methyl ester, having Rf = 0.44 on silica gel plates eluted with ethyl acetate-methylene chloride (1:4).

To the solution of 57 mg thereof in 1 ml of diethyl ether, 60 mg of 1-tri-n-butylphosphoranylidene-2-heptanone are added while stirring and the mixture is allowed to stand at room temperature overnight. It is evaporated, the residue subjected to preparative thin layer chromatography on silica gel plates, eluted with ethyl acetate-methylene chloride (2:23), to yield the 7-[3α-(3-oxo-1-trans-octenyl)-4β-(2-tetrahydropyranyloxy)-tetrahydro-2β-furyl]-5-cis-heptenoic acid methyl ester of the formula

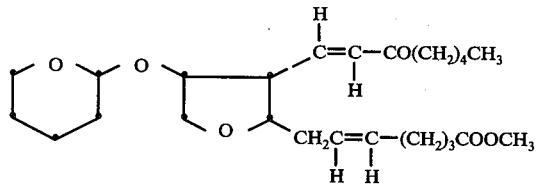

having Rf = 0.34 and showing in the NMR spectrum bands at 6.76, 6.18, 5.48 and 0.89 ppm.

EXAMPLE 5

To the solution of 0.617 g of 7-[3α-(3-oxo-1-trans-6-phenylhexenyl)-4β-(2-tetrahydropyranyloxy)-tetrahydro-2β-furyl]-heptanoic acid nitrile in 50 ml of ethanol, 0.167 g of sodium borohydride are added while stirring at 0°. After ½ hour, the mixture is poured into ice water, extracted with diethyl ether, the extract washed with water and saturated aqueous sodium chloride, dried and evaporated, to yield 0.59 g of 7-[3α-(3λ-hydroxy-1-trans-6-phenylhexenyl)-4β-(2-tetrahydropyranyloxy)-tetrahydro-2β-furyl]-heptanoic acid nitrile of the formula

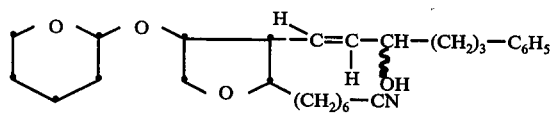

showing in the I.R. spectrum inter alia a band at 2253, but none at 1690 or 1630 cm$^{-1}$.

To the solution of 0.59 g thereof in 10 ml of methanol, 60 mg of p-toluene sulfonic acid are added and the mixture allowed to stand at room temperature overnight. The mixture is treated with 0.1 ml of triethylamine, evaporated, the residue taken up in water, the mixture extracted with diethyl ether, the extract washed with water and saturated aqueous sodium chloride, dried and evaporated. The residue is subjected to preparative thin-layer chromatography on silica gel plates (1 mm thick), eluted twice with ethyl acetatemethylene chloride (6.5:3.5) and of the two main fractions, the slower moving isomer is isolated, to yield the 7-[3α-(3β-hydroxy-1-trans-6-phenylhexenyl)-4β-hydroxy-tetrahydro-2β-furyl]-heptanoic acid nitrile of the formula

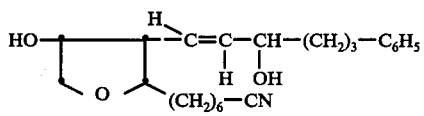

having an Rf = 0.22. (The corresponding 3α-hydroxy-compound has an Rf = 0.38).

The mixture of 0.22 g thereof, 7 ml of methanol, 3 ml of water and 1.5 ml of 20% aqueous potassium hydroxide is heated in a sealed tube to 115°–120° for 48 hours and evaporated. The residue is taken up in 20 ml of water and 20 ml of saturated aqueous sodium chloride, the mixture neutralized with dry ice and extracted 8 times with diethyl ether. The extract is dried and evaporated, to yield 0.18 g of 7-[3α-(3β-hydroxy-1-trans-6-phenylhexenyl)-4β-hydroxy-tetrahydro-2β-furyl]-heptanoic acid of the formula

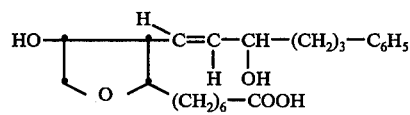

showing in the NMR spectrum bands at 7.2, 5.5, 3.78 and 2.63 ppm. The corresponding 7-[3α-(3α-hydroxy-1-trans-6-phenylhexenyl)-4β-hydroxy-tetrahydro-2β-furyl]-heptanoic acid is similarly prepared showing in the NMR spectrum bands at 7.2, 5.55, 4.1 and 1.35 ppm.

In the analogous manner the 7-[3α-(3-oxo-1-trans-6-phenylhexenyl)-4α-(2-tetrahydropyranyloxy)-tetrahydro-2β-furyl]heptanoic acid nitrile is converted to 7-[3α-(3β- and 3α-hydroxy-1-trans-6-phenylhexenyl)-4α-hydroxy-tetrahydro-2β-furyl]-heptanoic acid nitrile with Rf = 0.37 and 0.22 respectively [silica gel, ethyl acetate-methylene chloride(6.5:3.5)].

Both isomers are hydrolized with potassium hydroxide in methanol at 120° C for 48 hours and yield the 7-[3α-(3β- and 3α-hydroxy-1-trans-6-phenylhexenyl)-4α-hydroxy-tetrahydro-2β-furyl]heptanoic acids having an Rf = 0.60 and 0.57 respectively [silica gel, benzene-dioxane-acetic acid (10:10:0.5)].

The starting material is prepared as follows: To the solution of 0.935 g of 7-[3-formyl-4-(2-tetrahydropyranyloxy)tetrahydro-2-furyl)]-heptanoic acid nitrile in 40 ml of diethyl ether, 1.44 g of 1-tri-n-butyl-phosphoranylidene-2-(5-phenylpentanone) are added while stirring and the mixture allowed to stand at room temperature overnight. It is evaporated, the residue subjected to preparative thin-layer chromatography on silica gel plates (1 mm thick), twice eluted with ethyl acetate-methylene chloride (1:4), to yield the 7-[3α-(3-oxo-1-trans-6-phenylhexenyl)-4β-(2-tetrahydropyranyloxy)-tetrahydro-2β-furyl]-heptanoic acid nitrile of the formula

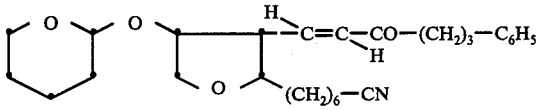

having Rf = 0.467.

The corresponding 4α-tetrahydropyranyloxy epimer has an Rf = 0.40.

EXAMPLE 6

The solution of 470 mg of 7-[3α-(3-oxo-1-trans-octenyl)-4β-(2-tetrahydropyranyloxy)-tetrahydro-2β-furyl]-heptanoic acid nitrile in 25 ml of dry tetrahydrofuran is cooled to −78° and 6 ml of a 1 molar solution of methylmagnesium iodide in tetrahydrofuran is added over a period of 2 minutes with stirring. After one hour, the excess of Grignard reagent is destroyed by adding 100 ml of wet diethyl ether. The mixture is washed with water, dried and evaporated. The residue is subjected to preparative thin-layer chromatography on silica gel plates (1 mm thick), eluted with ethyl acetate-methylene chloride (3:2) and the band corresponding to Rf = 0.49 yields the 7-[3α-(3β-hydroxy-3α-methyl-1-trans-octenyl)-4β-(2-tetrahydropyranyloxy)-tetrahydro-2β-furyl]-heptanoic acid nitrile.

The mixture of 361 mg thereof, 10 ml of methanol and 75 mg of oxalic acid is stirred at room temperature overnight. It is neutralized with triethylamine, 200 ml of ether are added, the mixture is washed with water, dried and evaporated, to yield the 7-[3α-(3β-hydroxy-3α-methyl-1-trans-octenyl)-4β-hydroxy-tetrahydro-2β-furyl]-heptanoic acid nitrile showing in the NMR spectrum bands at 5.68, 5.5, 4.18, 3.81, 3.52, 1.50 and 0.90 ppm.

The mixture of 165 mg thereof, 6 ml of methanol, 2 ml of water and 1 ml of 20% aqueous potassium hydroxide is heated in a sealed tube to 115°–120° for 48 hours and evaporated. The residue is taken up in 10 ml of water and 10 ml of saturated aqueous sodium chloride, the mixture neutralized with dry ice and extracted 8 times with diethyl ether. The extract is dried and evaporated, to yield the 7-[3α-(3β-hydroxy-3α-methyl-1-trans-octenyl)-4β-hydroxy-tetrahydro-2β-furyl]heptanoic acid of the formula

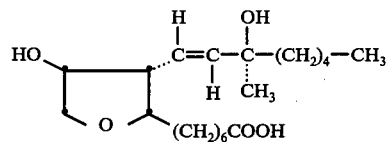

showing in the NMR spectrum bands at 6.29, 5.58, 2.31 and 0.90 ppm.

EXAMPLE 7

The solution of 100 mg of 7-[3α-(3β-hydroxy-1-trans-octenyl)-4β-hydroxy-tetrahydro-2β-furyl]heptanoic acid in 5 ml of diethyl ether is treated with excess of ethereal diazomethane at 0° for ½ hour and the solution evaporated under reduced pressure, to yield the corresponding methyl ester showing in the NMR spectrum bands at 3.64, 2.3 and 0.9 ppm.

In a similar manner the methyl esters of the acids illustrated by the examples are prepared, e.g. 7-[3α-(3β-hydroxy1-trans-nonenyl)-4β-hydroxy-tetrahydro-2β- furyl]heptanoic acid methyl ester showing in the NMR spectrum bands at 5.65, 2.3, 1.41 and 0.9 ppm.

EXAMPLE 8

56 mg of 7-[3α-(3β-hydroxy-1-trans-octenyl)-4β-hydroxytetrahydro-2β-furyl]-heptanoic acid are hydrogenated in 5 ml of ethanol over 10 mg of 10% palladium on charcoal at room temperature and atmospheric pressure. The catalyst is filtered off and the filtrate evaporated, to yield the 7-[3α-(3β-hydroxyoctyl)-4β-hydroxy-tetrahydro-2β-furyl]-heptanoic acid of the formula

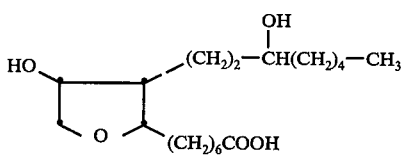

showing in the NMR spectrum bands of 3.8, 2.33, 1.31 and 0.9 ppm.

Analogously the unsaturated compounds of the remaining examples can be hydrogenated to the corresponding saturated compounds.

EXAMPLE 9

Analogous to the methods illustrated in the previous examples the following compounds of the formula

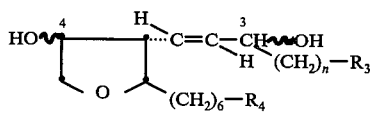

are prepared from equivalent amounts of the corresponding starting materials:

| No. | 4-OH | 3-OH | n | R₃ | Rf R₄=CN | Rf R₄=COOH |
|---|---|---|---|---|---|---|
| 1 | α | α | 5 | CH₃ | 0.27 A | 0.30 C |
| 2 | α | β | 5 | " | 0.43 A | 0.30 C |
| 3 | β | β | 5 | " | 0.26 B | 0.30 C |
| 4 | β | α | 5 | " | 0.38 B | 0.30 C |
| 5 | α | α | 6 | " | 0.38 B | 0.35 C |
| 6 | α | β | 6 | " | 0.55 B | 0.36 C |
| 7 | β | β | 6 | " | 0.28 B | 0.42 C |
| 8 | β | α | 6 | " | 0.43 B | 0.42 C |
| 9 | α | α | 2 | cyclopropyl | 0.28 A | 0.65 D |
| 10 | α | β | 2 | cyclopropyl | 0.46 A | 0.65 D |
| 11 | β | β | 2 | " | 0.25 A | 0.64 D |
| 12 | β | α | 2 | " | 0.38 A | 0.63 D |
| 13 | α | α | 3 | " | 0.263 A | 0.654 D |
| 14 | α | β | 3 | " | 0.425 A | 0.760 D |
| 15 | β | β | 3 | " | 0.275 A | 0.626 D |
| 16 | β | α | 3 | " | 0.434 A | 0.730 D |
| 17 | α | α | 2 | cyclopentyl | 0.27 A | 0.70 D |
| 18 | α | β | 2 | " | 0.42 A | 0.70 D |
| 19 | β | β | 2 | " | 0.225 A | 0.71 D |
| 20 | β | α | 2 | " | 0.325 A | 0.71 D |
| 21 | α | α | 2 | phenyl | 0.238 A | 0.61 D |
| 22 | α | β | 2 | " | 0.356 A | 0.64 D |
| 23 | β | β | 2 | " | 0.247 A | 0.59 D |
| 24 | β | α | 2 | " | 0.391 A | 0.66 D |

A = ethyl acetate-methylene chloride (13:7)
B = ethyl acetate-methylene chloride (3:2)
C = benzene - ethyl acetate-cyclohexane-methanol(10:10:2.5:2.5:0.1)
D = benzene - dioxane-acetic acid (2:2:0.1)

EXAMPLE 10

Preparation of injection ampuls each containing 50 mg of the active ingredient:

| Formula: | |
|---|---|
| 7-[3α-(3β-hydroxy-1-trans-octenyl)-4β-hydroxy-tetrahydro-2β-furyl]-heptanoic acid | 170 g |
| 1,1,1-Trichloro-2-methyl-2-propanol | 85 g |
| Polysorbate 80 | 85 g |
| Methylcellulose 100 cps | 1,785 g |
| Sodium carboxymethylcellulose 70 MV | 51 g |
| Water for injection | 17 lt. |

Procedure:

The chloropropanol is first dissolved in 13 lt of water at 90°, then the sodium carboxymethylcellulose is added while stirring, followed by the methylcellulose and stirring is continued for 15 minutes. The mixture is allowed to stand at 10° for 12 hours, combined with the polysorbate and the solution of the sodium chloride and active ingredient in 250 ml of water each. The resulting solution is made up to 17 lt with water, filtered through a sintered glass funnel, the filtrate placed into 2 lt sterilized bottles, steam-sterilixed at 100° for 3.25 hours and filled into 5 ml ampuls with standard equipment.

This injection solution ($10^{-2}$ g/ml) can be used in the preparation of an infusion solution, by adding the proper amount thereof to infusion saline, to obtain a solution containing 10 μg of the active ingredient per ml ($10^{-5}$ g/ml).

In the analogous manner injection- or infusion-solutions are prepared with the remaining compounds of the invention, especially those illustrated by the previous examples.

EXAMPLE 11

The solution of 250 mg of 7-[3α-(3-oxo-1-trans-octenyl)-4β-(2-tetrahydropyranyloxy)-tetrahydro-2β-furyl]-5-cis-heptenoic acid methyl ester in 5 ml of ethanol is cooled to 0°, 50 mg of sodium borohydride are added at once and the mixture is stirred at 0° for ½ hour. It is diluted with diethyl ether, washed with water dried and evaporated. The residue is dissolved in 2 ml of methanol, 15 mg of p-toluenesulfonic acid are added and the mixture is stirred at room temperature overnight. It is neutralized with triethylamine, evaporated and the residue chromatographed on silica gel and eluted twice with ethyl acetate-methylene chloride (1:1) to give the 7-[3α-(3β-hydroxy-1-trans-octenyl)-4β-hydroxytetrahydro-2β-furyl]-5-cis-heptenoic acid methyl ester having Rf=0.128; its 3α-isomer having Rf=0.335, and both compounds are identical with those obtained according to Example 4.

The starting material is prepared as follows: To the suspension of 7.15 g of methyl sodium glycolate in 50 ml of dimethylsulfoxide and 25 ml of diemthylformamide, cooled to 0°, are added at once 9.5 g of methyl 4,4-diethoxy-crotonate and the mixture is stirred at room temperature for 3 hours. It is poured into water, washed with diethyl ether and the aqueous layer is acidified with cold N hydrochloric acid. It is extracted twice with diethyl ether, the extract dried, evaporated and the residue distilled, to yield the methyl 2-diethoxymethyl-4-oxo-tetrahydrofuran-3-carboxylate boiling at 123°–126°/0.5 mm Hg.

The solution of 22.08 g thereof in 270 ml of ethanol and 270 ml of tetrahydrofuran is cooled to −70° and 3.4 g of sodium borohydride are added in portions over a period of 15 minutes. After stirring for 1 hour at −70° the mixture is diluted with diethyl ether, washed with water, dried and evaporated, Each gram of the residue is chromatographed on 100 g of silica gel and eluted with ethyl acetate-methylene chloride (1:4), to give the faster moving isomer of the methyl 2β-diethoxymethyl-4β-hydroxy-tetrahydrofuran-3α-carboxylate showing in the NMR-spectrum bands at 3.9, 3.75 and 1.25 ppm.

To the solution of 20.9 g thereof in 300 ml of tetrahydrofuran are added in portions 3.2 g of lithium aluminum hydride while stirring and maintaining the temperature at 0°. Stirring is continued for 1 hour, whereupon the mixture is diluted with diethyl ether, 9.6 ml of water are added dropwise. After stirring for 15 minutes it is filtered, the filtrate washed with water, dried and evaporated, to yield the 3α-hydroxymethyl-4β-hydroxytetrahydrofuran-2β-carboxaldehyde diethyl acetal showing NMR-bands at 4.5, 7.84 and 9.2 ppm.

The solution of 13.5 g thereof in 65 ml of pyridine is cooled to 0° and 19 g of benzoyl chloride are added dropwise. The mixture is stirred at room temperature for 3 hours, diluted with water and extracted with diethyl ether. The extract is washed with water, hydrochloric acid, water, dried and evaporated. Each gram of the residue is chromatographed on 30 g of silica gel using ethyl acetate methylene chloride (1:99) as eluent to give the corresponding dibenzoate showing in the NMR-spectrum bands at 5.75, 4.6 and 1.25 ppm.

The mixture of 14 g thereof, 150 ml of acetic acid and 100 ml of water is stirred at 70° for 24 hours and evaporated. The residue is taken up in diethyl ether, the solution washed with water, dried and evaporated. The residue is combined with the solution, made by adding 33 ml of 1.6 N n-butyl lithium dropwise to the suspension of 23 g of phenylthiomethyl-triphenylphosphonium chloride in 1 lt. of diethyl ether at 0°, and the mixture is stirred at 0° for ½ and at room temperature for 1 hour. It is poured into water, extracted with diethyl ether, the extract dried evaporated and each gram of the residue chromatographed on 30 g of silica gel using chloroform as eluent, to give the 2β-(2-phenylmercaptovinyl)-3β-benzoyloxymethyl-4β-benzoyloxy-tetrahydrofuran showing NMR-bands at 8.0, 7.3, 6.5 and 5.85 ppm.

The mixture of 200 mg thereof, 5 ml of methanol and 1 ml of 10% aqueous potassium carbonate is stirred at room temperature for 1 hour. The methanol is removed, the residue diluted with saturated aqueous sodium chloride and extracted three times with diethyl ether. The extract is dried, evaporated and the residue taken up in 5 ml of methylene chloride. The solution is treated with 100 mg of dihydropyrane and 10 mg of picric acid at room temperature overnight, washed with 10% aqueous potassium bicarbonate, dried and evaporated. The residue is subjected to preparative thin layer chromotography on silica gel plates and eluted with ethyl acetate-methylene chloride (1:4), to yield the 2β-(2-phenylmercaptovinyl)-3β-(2-tetrahydropyranyloxymethyl)-4β-(2-tetrahydropyranyloxy)-tetrahydrofuran having Rf=0.44.

The mixture of 79.4 mg thereof, 9 ml of glacial acetic acid, 0.6 ml of acetic anhydride and 1.2 g of mercuric acetate is stirred at 50° for 2 hours. It is evaporated, the residue taken up in 15 ml of methanol and the solution treated with 5 ml of 10% aqueous potassium carbonate at room temperature. The mixture is cooled to 0°, 500 mg of sodium borohydride are added and stirring is continued at 0° for 1 hour. It is evaporated, the residue diluted with water, extracted with diethyl ether, the extract dried and evaporated. The residue is subjected to preparative thin layer chromotography on silica gel plates and eluted with ethyl acetate, to yield the 2β-(2-hydroxyethyl)-3α-(2-tetrahydropyranyloxymethyl)-4β-(2-tetrahydropyranyloxy)-tetrahydrofuran having Rf=0.17.

To the solution of 270 mg thereof in 150 ml of methylene chloride, 1.2 g of chrominum dioxide-pyridine complex are added and the mixture is stirred at room temperature for 15 minutes. It is washed with water, dried, decolorized and evaporated, to yield the 2β-[3β-(2-tetrahydropyranyloxymethyl)-4β-(2-tetrahydropyranyloxy)-2β-tetrahydrofuryl]-acetaldehyde (NMR: 9.85, 4.6, 1.62 ppm).

The solution of 250 mg thereof in 1 ml of dimethylsulfoxide is added at once to that prepared by adding 3 ml of 1.5 N sodium methylsulfinylmethide in dimethylsulfoxide to the solution of 1.1 g of 4-carbomethoxybutyl-triphenylphosphonium chloride in 5 ml of dimethylsulfoxide and stirring the mixture for 10 minutes. The whole is stirred at room temperature for one hour, water is added and the mixture extracted with diethyl ether twice. The extract is washed with water, dried and evaporated. The residue is taken up in diethyl ether and the solution treated with a slight excess of diazomethane. The solution is decolorized with charcoal and evaporated to yield the 7-[3α-(2-tetrahydropyranyloxymethyl)-4β-(2-tetrahydropyranyloxy)-2β-tetrahydrofuryl]-5-cis-heptenoic acid methyl ester.

The mixture of 167 mg thereof, 5 ml of methanol and 10 mg of p-toluenesulfonic acid is stirred at room temperature overnight. The acid is neutralized with triethylamine, the mixture evaporated, the residue taken up in diethyl ether, the solution washed with water, dried and evaporated. The residue is chromatographed on silica gel plates and eluted with ethyl acetate, to yield the 7-(3α-hydroxymethyl-4β-hydroxy-2β-tetrahydrofuryl)-5-cis-heptenoic acid methyl ester having Rf=0.235.

The solution of 88 mg thereof in 1 ml of pyridine is cooled to 0°, 70 mg of p-nitrobenzoyl chloride are added and the mixture is stirred at 0° for 4 hours and at room temperature overnight. It is diluted with water, extracted with diethyl ether, the extract washed with water, cold N hydrochloric acid, again with water, dried and evaporated. The residue is subjected to preparative thin layer chromatography on silica gel plates and eluted with ethyl acetate-methylene chloride (1:4) and the band with Rf=0.187 yields the 7-(3α-p-nitrobenzoyloxymethyl-4β-hydroxy-2β-tetrahydrofuryl)-5-cis-heptenoic acid methyl ester.

The mixture of 55 mg thereof, 1 ml of methylene chloride 15 mg of dihydropyrane and 5 mg of picric acid is stirred at room temperature overnight. It is diluted with diethyl ether, washed with 10% aqueous potassium bicarbonate, water, dried and evaporated. The residue is chromatographed on silica gel plates and eluted with ethyl acetate-methylene chloride (1:4), to give the 7-[3α-p-nitrobenzoyloxymethyl-4β-(2-tetrahydropyranyloxy)-2β-tetrahydrofuryl)-5-cis-heptenoic acid methyl ester having Rf=0.28.

The mixture of 75 mg thereof, 1 ml of methanol and 0.1 ml of 10% aqueous potassium carbonate is stirred at room temperature for 10 minutes. It is diluted with diethyl ether, washed with water, dried and evaporated. The residue is chromotographed on silica gel and eluted with ethyl acetate-methylene chloride (1:4), to yield the 7-[3α-hydroxymethyl-4β-(2-tetrahydropyranyloxy)-2β-tetrahydrofuryl)-5-cis-heptenoic acid methyl ester having Rf=0.143.

To the solution of 60 mg thereof in 30 ml of methylene chloride, 270 mg of chromium trioxide-pyridine complex are added and the mixture is stirred at room temperature for 15 minutes. It is washed with water, decolorized with charcoal, dried and evaporated to yield the 7-[3α-formyl-4β-(2-tetrahydropyranyloxy)-2β-tetrahydrofuryl]-5-cis-heptenoic acid methyl ester having Rf=0.44 on silica gel plates eluted with ethyl acetate-methylene chloride (1:4).

The mixture of 51 mg thereof, 60 mg tributyl-phosporanylidene-2-heptanone and 1 ml of diethyl ether is stirred at room temperature overnight. It is evaporated, the residue chromatographed on silica gel plates and eluted with ethyl acetate-methylene chloride (2:23), to yield the 7-[3α-(3-oxo-1-trans-octenyl)-4β-(2-tetrahydropyranyloxy)-tetrahydro-2β-furyl]-5-cis-heptenoic acid methyl ester having Rf=0.34.

EXAMPLE 12

According to the methods illustrated by the previous examples the following compounds of Formula I are prepared from equivalent amounts of the corresponding starting materials: $A=(CH_2)_2$, $R=R_2=H$, $R_1=$ trans-H, Rf-values of acids on silica gel, eluted with benzene-dioxane-ethyl acetate (20:20:1); Rf of nitriles on silica gel, eluted with ethyl acetate-methylene chloride (13:7).

| No. | 4-OH | chain 3-OH | $R_3$ | Rf= | Rf-nitrile |
|---|---|---|---|---|---|
| 1 | β | β | benzyl | 0.44 | 0.41 |
| 2 | β | α | " | 0.48 | 0.55 |
| 3 | α | α | " | 0.45 | 0.38 |
| 4 | α | β | " | 0.45 | 0.51 |
| 5 | β | β | p-CH$_3$O-C$_6$H$_4$-(CH$_2$)$_2$ | | |
| 6 | β | α | " | 0.49 | 0.39 |
| 7 | α | α | " | 0.43 | 0.25 |
| 8 | α | β | " | 0.53 | 0.40 |
| 9 | β | β | o-F-C$_6$H$_4$-(CH$_2$)$_2$ | 0.46 | 0.37 |
| 10 | β | α | " | 0.53 | 0.51 |
| 11 | α | α | " | 0.44 | 0.35 |
| 12 | α | β | " | 0.46 | 0.50 |
| 13 | β | β | m-F-C$_6$H$_4$-(CH$_2$)$_2$ | 0.53 | 0.27 |
| 14 | β | α | " | 0.50 | 0.39 |
| 15 | α | α | " | 0.51 | 0.25 |
| 16 | α | β | " | 0.51 | 0.37 |
| 17 | β | β | p-F-C$_6$H$_4$-(CH$_2$)$_2$ | 0.42 | 0.35 |
| 18 | β | α | " | 0.46 | 0.49 |
| 19 | α | α | " | 0.42 | 0.33 |
| 20 | α | β | " | 0.49 | 0.46 |
| 21 | β | β | p-Cl-C$_6$H$_4$-(CH$_2$)$_2$ | 0.42 | 0.28 |
| 22 | β | α | " | 0.47 | 0.41 |
| 23 | α | α | " | 0.45 | 0.31 |
| 24 | α | β | " | 0.45 | 0.43 |
| 25 | β | β | m-CF$_3$-C$_6$H$_4$-O-CH$_2$ | 0.439 | — |
| 26 | β | α | " | 0.461 | — |
| 27 | α | α | " | 0.463 | — |
| 28 | α | β | " | 0.425 | — |

EXAMPLE 13

Preparation of 10,000 tablets each containing 50.0 mg of the active ingredient:

| Formula: | |
|---|---|
| 7-[3α-(3β-hydroxy-1-trans-5-o-fluorophenylpentenyl)-4α-hydroxy-tetrahydro-2β-furyl]-heptanoic acid (Ex. 12, No. 12) | 500.00 g |
| Lactose | 1,706.00 g |
| Corn starch | 90.00 g |
| Polyethylene glycol 6,000 | 90.00 g |
| Talcum powder | 90.00 g |
| Magnesium stearate | 24.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 45 ml of water and the suspension added to the boiling solution of the polyethylene glycol in 180 ml of water. The paste formed is added to the powders which are granulated, if necessary, with an additional amount of water. The granulate is dried overnight at 35°, broken on a screen with 1.2 mm openings and compressed into tablets using concave punches with 7.1 mm diameter, uppers bisected.

Analogously tablets are prepared from the other compounds illustrated herein, e.g. those of Formula II.

EXAMPLE 14

According to the methods illustrated by the previous examples, e.g. Examples 1, 4 and 11, the following compounds of Formula II are obtained from equivalent amounts of the corresponding starting materials:

| $R_4 = R_5 = H$ | | Chain | | | |
|---|---|---|---|---|---|
| No. | 4-OH | 3-OH | A | $R_6$ | $R_f=$ |
| 1 | β | β | cis-(CH$_2$)$_2$ | o-F-C$_6$H$_4$-(CH$_2$)$_2$ | 0.474 |
| 2 | β | α | " | " | 0.576 |
| 3 | α | α | " | " | 0.466 |
| 4 | α | β | " | " | 0.520 |
| 5 | β | β | (CH$_2$)$_2$ | o-CF$_3$-C$_6$H$_4$-(CH$_2$)$_2$ | 0.458 |
| 6 | β | α | " | " | 0.519 |
| 7 | α | α | " | " | 0.464 |
| 8 | α | β | " | 0.482 | |
| 9 | β | β | " | ⟨O⟩-(CH$_2$)$_2$ | 0.460 |
| 10 | β | α | " | " | 0.477 |
| 11 | α | α | " | " | 0.456 |
| 12 | " | β | " | " | 0.500 |
| 13 | β | β | " | m-CF$_3$-C$_6$H$_4$-(CH$_2$)$_2$ | 0.600 |
| 14 | β | α | " | " | 0.688 |
| 15 | α | α | " | " | 0.656 |
| 16 | α | β | " | " | 0.675 |

$R_f$'s are measured on silica gel plates eluted with benzene dioxane-acetic acid (2:2:0.1).

EXAMPLE 15

Compound No. 25 of Example 12 can also be prepared by the following slightly modified process: The mixture of 56 g of 7-[3-hydroxymethyl-4-(2-tetrahydropyranyloxy)-tetrahydro-2-furyl]-heptanoic acid nitrile U.S. Pat. No. 3,883,659, Column 13), 150 ml of methanol, 75 ml of water and 75.5 ml of 20% aqueous potassium hydroxide is heated in a sealed tube to 115°–120° for 48 hours and evaporated. The residue is taken up in 100 ml of water and 100 ml of saturated aqueous sodium chloride, the mixture neutralized with dry ice and extracted 6 times with diethyl ether. The extract is dried, evaporated, the residue dissolved in diethyl ether and heated with ethereal diazomethane until the discoloration ceases. The mixture is evaporated, to give the 7-[3-hydroxymethyl-4-(2-tetrahydropyranyloxy)-tetrahydro-2-furyl]-heptanoic acid methyl ester.

To the solution of 13 g thereof in 2 lt. of methylene chloride, 61 g of pyridine chromiun trioxide complex are added at once and the mixture is stirred at room temperature for 15 minutes. It is washed with water, dried, treated with charcoal, filtered and evaporated, to yield the 2-(6-carbomethoxyhexyl)-4-(2-tetrahydropyranyloxy)-tetrahydrofurane-3-carboxaldehyde.

The solution of 12.07 g thereof in 25 ml of dimethoxyethane is added at once to the solution made by adding 13.7 g of dimethoxy-[3-(m-trifluoromethylphenoxy)-2-oxo-propyl]-phosphonate to the suspension of 1.68 g of sodium hydride in 280 ml of dimethoxyethane, and stirring the mixture for two hours. The whole mixture is stirred at room temperature overnight and evaporated. The residue is taken up in diethyl ether and the solution washed with water. The organic layer is dried, evaporated and the residue subjected to preparative thin layer chromatography on silica gel plates (1 mm thick), which are eluted with ethyl acetate-methylene chloride (1:4), to yield the 7-[3α-(3-oxo-4-(m-trifluoromethylphenoxy)-1-trans-butenyl)-4β-(2-tetrahydropyranyloxy)-tetrahydro-2β-furyl]-heptanoic acid methyl ester, having Rf = 0.5. (The corresponding 4α-tetrahydropyranyloxy epimer has Rf = 0.43).

To a solution of 4.74 g thereof in 100 ml of ethanol, 1.02 g of sodium borohydride are added while stirring at 0°. After 1/2 hour, the mixture is poured into ice-water, extracted with diethyl ether, the extract washed with water and saturated aqueous sodium chloride, dried and evaporated, to yield the 7-[3α-(3-hydroxy-4-(m-trifluoromethylphenoxy)-1-trans-butenyl)-4β-(2-tetrahydropyranyloxy)-tetrahydro-2β-furyl]-heptanoic acid methyl ester.

To the solution of 4.54 g thereof in 50 ml of methanol, 50 mg of p-toluenesulfonic acid are added and the mixture allowed to stand at room temperature overnight. It is evaporated, the residue taken up in water, the mixture extracted with diethyl ether, the extract washed with water and saturated aqueous sodium chloride, dried and evaporated. The residue is chromotographed on 200 g of silica gel and eluted with ethyl acetate-methylene chloride (1:1). Of the two main fractions the slower moving isomer is the 7-[3α-(3β-hydroxy-4-(m-trifluoromethylphenoxy)-1-trans-butenyl)-4β-hydroxy-tetrahydro-2β-furyl]-heptanoic acid methyl ester.

The mixture of 1.75 g thereof, 18 ml of methanol and 6 ml of N aqueous, sodium hydroxide is stirred at room temperature overnight, and evaporated. The residue is taken up in 20 ml of water and 20 ml of saturated aqueous sodium chloride, neutralized with N hydrochloric acid and extracted 5 times with diethyl ether. The extract is dried and evaporated, to yield the 7-[3α-(3β-hydroxy-4-(m-trifluoromethylphenoxy)-1-trans-butenyl)-4β-hydroxy-tetrahydro-2β-furyl]-heptanoic acid of the formula

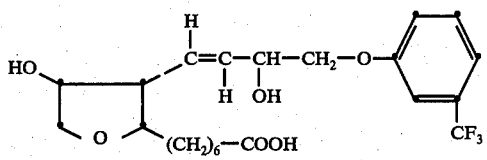

having Rf = 0.439 on silica gel eluted with benzene-dioxaneacetic acid (10:10:0.5).

The corresponding 3α-hydroxy-epimer is analogously synthesized from the corresponding ester and has Rf = 0.461.

The corresponding 4α,3β- and 4α,3α-dihydroxy-analogs have Rf = 0.463 and 0.425 respectively.

EXAMPLE 16

Preparation of 1,000 capsules each containing 20 mg of the active ingredient:

| Formula: | |
|---|---|
| 7-[3α-(3β-hydroxy-1-trans-4-m-trifluorophenoxy-butenyl)-4β-hydroxy-tetrahydro-2β-furyl]-heptanoic acid | 20.00 g |
| Lactose | 265.00 g |
| Talcum powder | 15.00 g |

Procedure:

All the powders are passed through a screen with openings of 0.6 mm. Then the drug substance is placed in a suitable mixer and mixed first with the talcum, then with the lactose until homogeneous. No. 2 hard gelatin capsules are filled with 300 mg each, using a capsule filling machine.

Analogously capsules are prepared from the other compounds illustrated herein.

I claim:

1. A 7-[3α-hydroxy-(3-hydrocarbylpropyl or -1-propenyl)-4-hydroxy-tetrahydro-2β-furyl]-heptanoic or 5-heptenoic acid of the formula

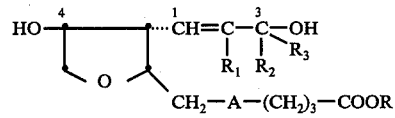

wherein each of R and $R_3$ is lower alkyl, lower alkenyl, lower alkynyl, (3 to 7 ring-membered cycloalkyl or cycloalkenyl)-$C_mH_{2m}$ wherein m is an integer from 0 to 4, (Ph, PhO or Hc)-$C_nH_{2n}$, wherein Ph is phenyl, (lower alkyl)-phenyl, (lower alkoxy)-phenyl, (lower alkylenedioxy)-phenyl, (halogeno)-phenyl, (trifluoromethyl)-phenyl,(nitro)-phenyl or (di-lower alkylamino)-phenyl, Hc is furyl or thienyl and n is an integer from 1 to 4, R is also hydrogen, an alkali metal or one equivalent of an alkaline earth metal and $R_3$ is also (lower alkoxy or halo)-lower alkyl, A is ethylene or ethenylene, $R_1$ and $R_2$ are hydrogen or lower alkyl, or the 1,2-dihydro-derivatives thereof.

2. A compound as claimed in claim 1 and corresponding to the formula

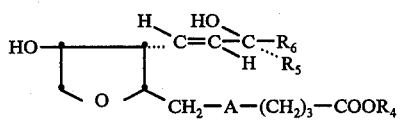

wherein $R_4$ is hydrogen, sodium, potassium or alkyl with up to 4 carbon atoms, A is ethylene or cis-ethenylene, $R_5$ is hydrogen or methyl and $R_6$ is n-(pentyl, pent-2-enyl, hexyl or heptyl), (cyclopropyl, cyclopentyl, cyclohexyl, Ph', Ph'O or 2-furyl)-methyl or -ethyl, wherein Ph' is phenyl, tolyl, anisyl, fluorophenyl, chlorophenyl or trifluoromethylphenyl, or their 4α-hydroxy-isomers.

3. A compound claimed in claim 2, in which formula $R_4$ is hydrogen, sodium or potassium, A is ethylene or cis-ethenylene, $R_5$ is hydrogen or methyl and $R_6$ is n-pentyl, n-hexyl, 2-o-fluorophenethyl or m-trifluoromethylphenoxymethyl.

4. A compound as claimed in claim 2, and being the 7-[3α-(3β-hydroxyl-1-trans-octenyl-4β-hydroxy-tetrahydro-2β-furyl]-heptanoic acid.

5. A compound as claimed in claim 2, and being the 7-[3α-(3β-hydroxy-1-trans-octenyl)-4β-hydroxy-tetrahydro-2β-furyl]-5-cis-heptenoic acid.

6. A compound as claimed in claim 3, and being the 7-[3α-(3β-hydroxy-1-trans-4-m-trifluorophenoxy-butenyl)-4β-hydroxy-tetrahydro-2β-furyl]-heptanoic acid.

7. A pharmaceutical composition comprising a compound of the formula

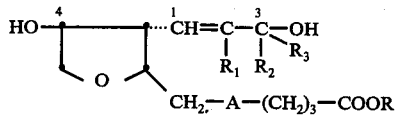

wherein R is hydrogen, an alkali metal or one equivalent of an alkaline earth metal, or lower alkyl, lower alkenyl, lower alkynyl, (3 to 7 ring-membered cycloalkyl or cycloalkenyl)—$C_mH_{2m}$ wherein $m$ is an integer from 0 to 4, (Ph, PhO or Hc)—$C_nH_{2n}$, wherein Ph is phenyl, (lower alkyl)-phenyl, (lower alkoxy)-phenyl, (lower alkylenedioxy)-phenyl, (halogeno)-phenyl, (trifluoromethyl)-phenyl, (nitro)-phenyl or (di-lower alkylamino)-phenyl, Hc is furyl or thienyl and $n$ is an integer from 1 to 4, A is ethylene or ethenylene, $R_1$ and $R_2$ are hydrogen or lower alkyl, and $R_3$ is (PhO or Hc)-$C_nH_{2n}$, or the 1,2-dihydro-derivatives thereof, in an amount sufficient for producing a prostaglandin-like effect, together with a pharmaceutical excipient.

8. A method for the reduction of hypertension and fertility in mammals, which consists in administering to said mammals a composition as claimed in claim 7.

* * * * *